United States Patent [19]

Sanderson et al.

[11] Patent Number: 5,176,502

[45] Date of Patent: Jan. 5, 1993

[54] SYRINGE PUMP AND THE LIKE FOR DELIVERING MEDICATION

[75] Inventors: George G. Sanderson, Clark; Mario Massaglia, Andover; Mitchell J. Palmer, Succasunna, all of N.J.

[73] Assignee: Becton, Dickinson and Company, Franklin Lakes, N.J.

[21] Appl. No.: 514,187

[22] Filed: Apr. 25, 1990

[51] Int. Cl.[5] ............... F04B 17/02; F04B 49/00
[52] U.S. Cl. ................................ 417/18; 417/415
[58] Field of Search ............. 417/18, 415; 604/30, 604/65, 66, 67, 155; 128/DIG. 12, DIG. 13, DIG. 1

[56] References Cited

U.S. PATENT DOCUMENTS

| | | |
|---|---|---|
| 3,623,474 | 11/1971 | Heilman et al. |
| 3,701,345 | 10/1972 | Heilman et al. |
| 4,191,187 | 3/1980 | Wright ........................... 604/155 |
| 4,529,401 | 7/1985 | Leslie et al. ..................... 604/155 |
| 4,741,732 | 5/1988 | Crankshaw et al. |
| 4,767,406 | 8/1988 | Wadham et al. .................. 604/155 |
| 4,804,368 | 2/1989 | Skakoon et al. .................. 604/155 |
| 4,838,857 | 6/1989 | Strowe et al. |
| 4,931,041 | 6/1990 | Faeser. |
| 4,976,696 | 12/1990 | Sanderson et al. ............... 604/65 |

Primary Examiner—Richard A. Bertsch
Assistant Examiner—Alfred Basichas
Attorney, Agent, or Firm—Aaron Passman; Michael G. Schwarz

[57] ABSTRACT

A syringe pump comprises a housing with a syringe retainer. The syringe includes a barrel for liquid medication and a plunger movably positioned in the barrel for expelling the medication. A driver is movably mounted on the housing for engagement with the plunger. A control mechanism within the housing regulates the rate of movement of the driver and plunger during delivery of medication. A monitoring circuit connected to receive signals from a potentiometer and a movable contact associated with the driver indicates driver motion. A microprocessor with memory includes a preset standard to which the signal of motion from the driver is compared. An additional input signal, of motion from a rotary indicator associated with a part of the driver movement motor assembly, is provided to the memory and is compared to plunger travel into the barrel.

5 Claims, 5 Drawing Sheets

SYRINGE PUMP AND THE LIKE FOR DELIVERING MEDICATION

BACKGROUND OF THE INVENTION

1. Field of the Invention

The present invention relates to a device to deliver or administer medication to a patient, and more particularly, concerns a syringe pump monitoring circuit intended for the controlled delivery or administration of such medications.

2. Background Description

Hospitals typically use intravenous (I.V.) administration sets to deliver liquid medication to patients. When the patient needs medication, such as an antibiotic, standard practice until recently has been to deliver such a drug by a "piggy-back" drip into the primary infusion line. Recently, however, the procedure for delivering antibiotics and other drugs to patients on I.V. therapy has been changing. Mechanically driven syringes, frequently called or referred to as syringe pumps, are available to hospitals and other users for the administration of drugs and other liquid medications which the patient may require.

Indeed, a wide variety of syringe pumps and other liquid medication delivery devices are becoming available. With particular reference to a syringe pump, as that term is used herein, such pump employs a conventional or modified syringe which holds the liquid medication, the plunger of which is typically driven or pushed by a mechanized element for the automatic delivery of the liquid contents within the syringe. These syringe pumps are now available in battery powered form, include microprocessor technology for programming rates or times of medication delivery, have digital displays for ease of viewing by the user or the patient, include alarm circuits in the event of duty cycle completion, failure, or line occlusion, and other features to facilitate the operation or performance of the syringe pump. As these syringe pumps become more sophisticated, the technological advances frequently have the tendency to increase the expense of making and using the device, increase the complexity of use, and increase the opportunities for breakdown and repair if one or more of the operational elements fail.

For example, many existing syringe pumps include an occlusion circuit for producing an alarm (visual and/or audible) when the syringe cycle has been completed, if the I.V. line or syringe is occluded or if there is a system failure. One common mechanism for activating the occlusion circuit has been the use of one or more switches which are tripped after the syringe plunger passes a certain point during its travel into the syringe barrel. In other instances, the syringe is mounted on a spring loaded platform which is subject to a small linear movement after a certain force level has been reached. Thus, if the plunger being pushed into the syringe barrel either reaches the bottom of the syringe or cannot expel the liquid contents due to an occlusion in the line, the force against the plunger causes the entire spring-mounted syringe to move in linear fashion. This movement, in turn, either trips a switch or may be sensed by position sensitive sensors to send a signal to the occlusion circuit so that the automatic operation of the syringe pump may be terminated.

Improvements in such a plunger movement monitoring circuits are not only desirable, but are still being sought, in order to reduce the expense of the elements heretofore needed in such an occlusion circuit, as well as to eliminate the need for switches or sensing elements in order to achieve the desired results and make the syringe pump fail safe.

Rate feedback measurements for syringe pumps have been obtained from a tachometer gear driven off of the injector drive motor. The output voltage from the tachometer corresponds to the velocity of fluid flowing due to the pressure generated in the syringe pump. In the event that the tachometer became disengaged from the motor or the motor stopped, the voltage produced could approach zero and be indistinguishable from noise and interference, thus resulting in errors and inaccuracies.

In order to overcome the problems of velocity of flow measurement obtained from a gear driven tachometer, artisans have used a plunger position feedback signal generated by a potentiometer mechanically driven by the syringe motor. Such systems have been designed to use a rotary potentiometer which is drivingly connected to the motor output, such that as the motor shaft turns a corresponding gear drives the potentiometer to produce a direct measurement of shaft rotation. Since the motor is connected through means of a ball nut to the syringe plunger, the potentiometer should properly read the position of the plunger. This is not the case however if an overload conditions occurs or if for some reason the motor gear drive to the potentiometer fails. Therefore, it is desired that the gear drive interconnection of the potentiometer be eliminated in order to be certain that the exact position of the plunger is known.

It is toward such improvements, as mentioned already, as well as other improvements as will be pointed out, that the present invention is directed.

SUMMARY OF THE INVENTION

The syringe pump of the present invention comprises a housing and a retainer mounted thereon for receiving a syringe. The syringe to be received is of the type including a barrel for holding liquid medication and a plunger movably positioned in the barrel for expelling liquid medication therefrom. A driver is movably mounted on the housing for engagement with the plunger and for pushing the plunger into the barrel to thereby force the liquid medication out of the barrel. A control within the housing regulates the rate of movement of the driver against the plunger to thereby provide the delivery of the liquid medication from the barrel. Depressible actuation switches are mounted on the housing for manual access by a user. The actuation switches are associated with the control to permit the user to select one or more functions under which the control operates. The actuation switches are connected to the control when depressed by the user to electrically energize or de-energize the control for the operation of the selected function.

In the preferred embodiment of the present invention, the control includes an electrically powered motor for moving the driver. A monitoring circuit is provided to assess the motion of the driver and a part of the motor during delivery of liquid medication from the barrel. This monitoring circuit is responsive to inputs from a linear potentiometer. The linear potentiometer with an electrically conductive strip of resistive material positioned to be engaged with a contact carried by the driver and in circuit with the control provides the input signal to the monitoring circuit. A changing voltage, varying as a function of plunger displacement, provides the monitoring circuit with an input signal as to plunger position and movement.

A rotary indicator associated with the motor part and responsive to its rotary movement signals the monitoring circuit providing an additional input of a series of pulses to report the position and movement of the part of the motor assembly such that uniformly spaced pulses indicate the constant rotation of the part of the motor. The monitoring circuit is mounted on the housing and connected to the linear potentiometer and the rotary indicator to receive the input signal from the linear potentiometer and to receive the additional input signal from the rotary indicator so the driver motion relative to rotation of the part of the motor can be compared to a preset delivery of liquid medication from the barrel.

It is a feature of the present invention that the syringe plunger movement be automatically measured or sensed so that motion related information may be provided to a microprocessor part of the monitoring circuit. The input from the linear potentiometer is in the preferred embodiment a linearly decreasing voltage which relates directly to plunger position. That is to say that the voltage starts high and preferably decreases at a constant rate with respect to plunger travel. The position and the change is a function of voltage over time and that is directly related to the rate of medication delivered. Consequently, motion of the plunger is constantly monitored from the varying voltage obtained from the linear potentiometer.

A further advantage and improvement is provided by the present invention in the circuit used to monitor plunger movement as the driver pushes the plunger into the syringe barrel. In known and existing syringe pumps, the driver is typically coupled by a half-nut arrangement to a lead screw which is rotated by the motor and the occlusion or position responsive devices are connected to provide information relative to the speed of rotation or the lack of motor movement. The present monitoring circuit verifies that the lead screw is rotated a set rate and the plunger is moving at the preset rate. The monitoring circuit compares the varying voltage signal received from the linear potentiometer with a voltage profile in the memory of the monitoring circuit and with the additional input of uniformly spaced pulses from the rotary indicator. An alarm is activated if the comparison of the linear potentiometer voltage due to plunger movement or the rotation of the motor part are not as they should be.

In presently known and available syringe pumps, features for detecting syringe plunger motion were designed to signal occlusion and not verify programmed motion of the driver and the uniform rotary motion of the motor part. In the delivery of drugs which are necessary to maintain life, the importance of monitoring the plunger movement to verify delivery is needed to maintain life support. The preferred arrangement minimizes manufacturing steps as well as simplifying the design and operation of the syringe pump motion monitoring circuit.

Other advantages, improvements and features of the present invention will be apparent upon reading the detailed description.

DETAILED DESCRIPTION

While this invention is satisfied by embodiments in many different forms, there is shown in the drawings and will herein be described in detail a preferred embodiment of the invention; with the understanding that the present disclosure is to be considered as exemplary of the the principles of the invention and is not intended to limit the invention to the embodiment illustrated. The scope of the invention will be measured by the appended claims and their equivalents.

Figure 1:
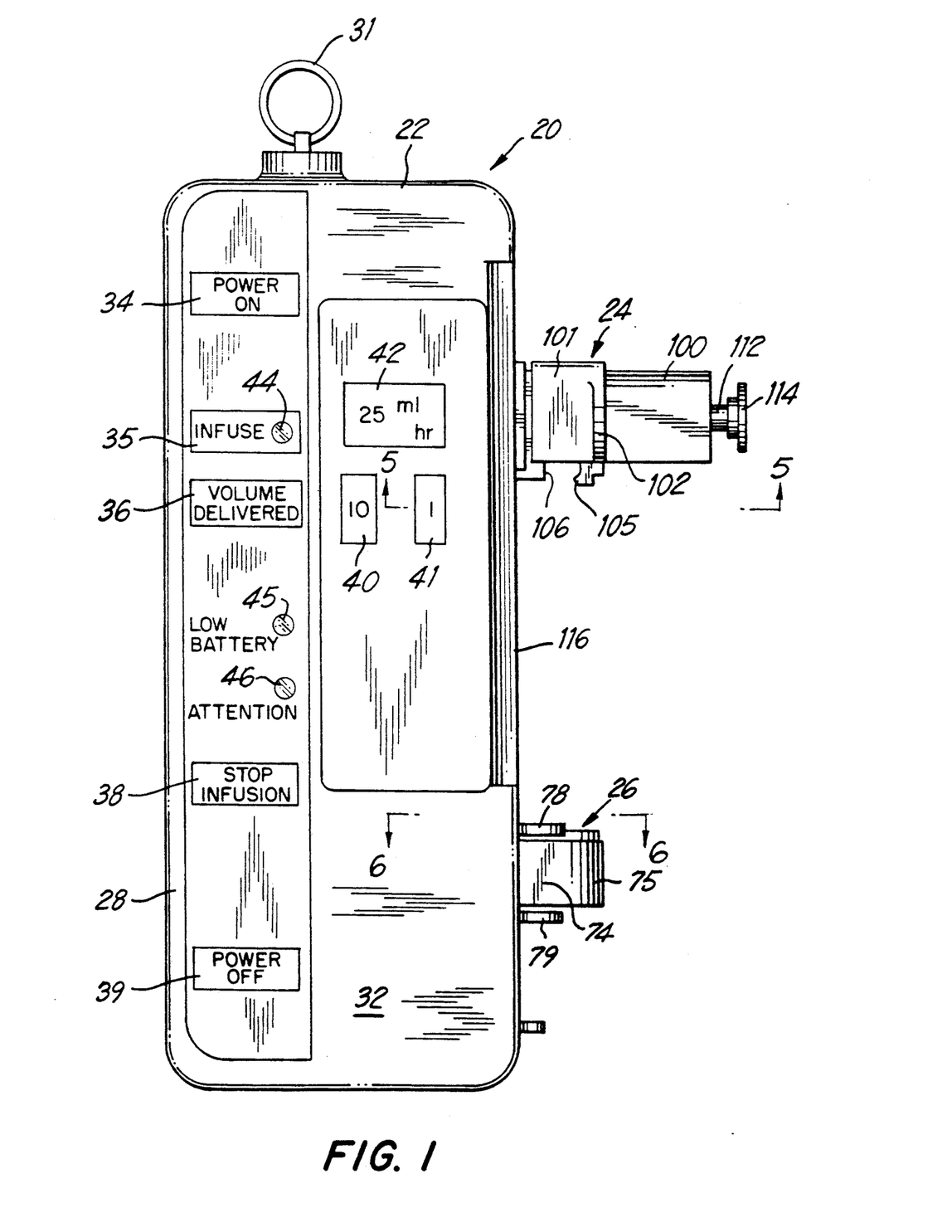
FIG. 1 is a plan view of the preferred embodiment of the syringe pump of the present invention illustrating the front face thereof as it appears to a user.
Figure 2:
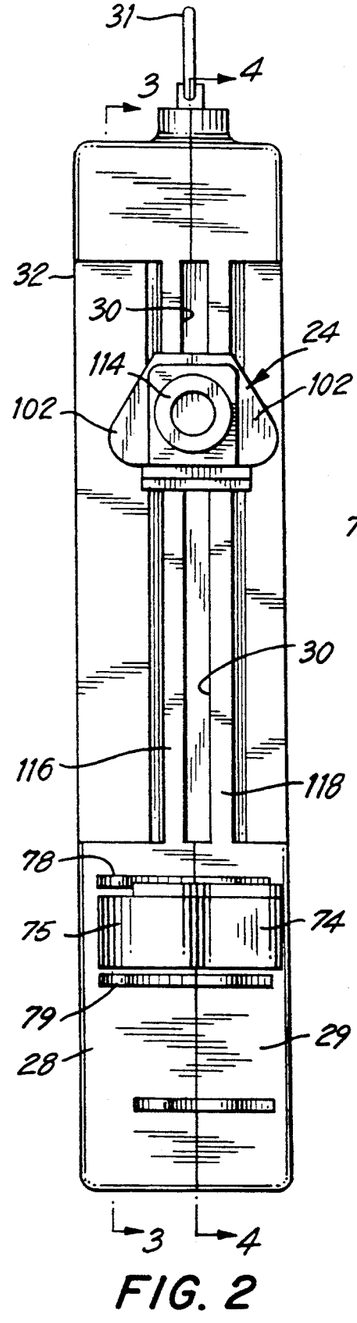
FIG. 2 is a side view of the syringe pump of FIG. 1 looking toward the side having the driver for moving the plunger and the retainer for mounting the syringe barrel.

Turning to the drawings, and FIGS. 1 and 2 in particular, there is shown a syringe pump 20 in a preferred configuration for purposes of the present invention. In general, syringe pump 20 is comprised of a housing 22, a driver mechanism 24 and a syringe retainer 26. In the preferred configuration, housing 22 is a compact, lightweight housing which is assembled in two parts, consisting of an upper (front) cover 28 and a lower (back) cover 29. Each of covers 28 and 29 is preferably formed in tray-like fashion so as to be able to include the interior components of the syringe pump, as well as for ease of assembly with a few screws or the like. When assembled, it is preferred that covers 28 and 29 form housing 22 which is completely enclosed except for an elongate slot 30 on one side of the housing. This slot, as will be described more fully hereinafter, permits driver mechanism 24 to move outside of the housing while being driven by a motor and drive carried within the housing. A ring 31 is connected to the housing to provide a place for hanging the syringe pump on a stand at the location where the patient is to receive the mediation from the syringe pump.

Upper cover 28 includes a front face 32 with a number of controls and displays. It is understood that many different controls or displays may be provided in syringe pump 20 depending upon a variety of factors and intended functions thereof. For purposes of the present invention, and while suggesting no limitations, upper face 32 includes five control mechanisms or buttons, namely, "POWER ON" 34, "INFUSE" 35, "VOLUME DELIVERED" 36, "STOP INFUSION" 38, and "POWER OFF" 39. Two other buttons or controls are provided, one such button 40 permitting the user to increment the rate of medication delivery by "1's." When buttons 40 and 41 are depressed by the user, a display 42 digitally indicates the numbers that have been incrementally selected by the user. Each time buttons 40 and 41 are pushed, the digit in the "1's" or "10's" columns are incremented by one until the number selected by the user is displayed. In the embodiment being described, display 42 usually shows the rate of delivery of medication, in milliliters per hour, to be selected by the user.

In addition to display 42, INFUSE button 35 has a light display 44 associated therewith so that the light is turned on when the INFUSE button has been pushed to inform the user that infusion is taking place. Another panel light 45 is provided to indicate when the batteries are low. A third panel light 46 is provided as an ATTENTION indicator serving as a visual alarm to inform the user that the syringe is empty, the plunger motion is not correct or that an occlusion has occurred and infusion has been terminated.

Figure 3:
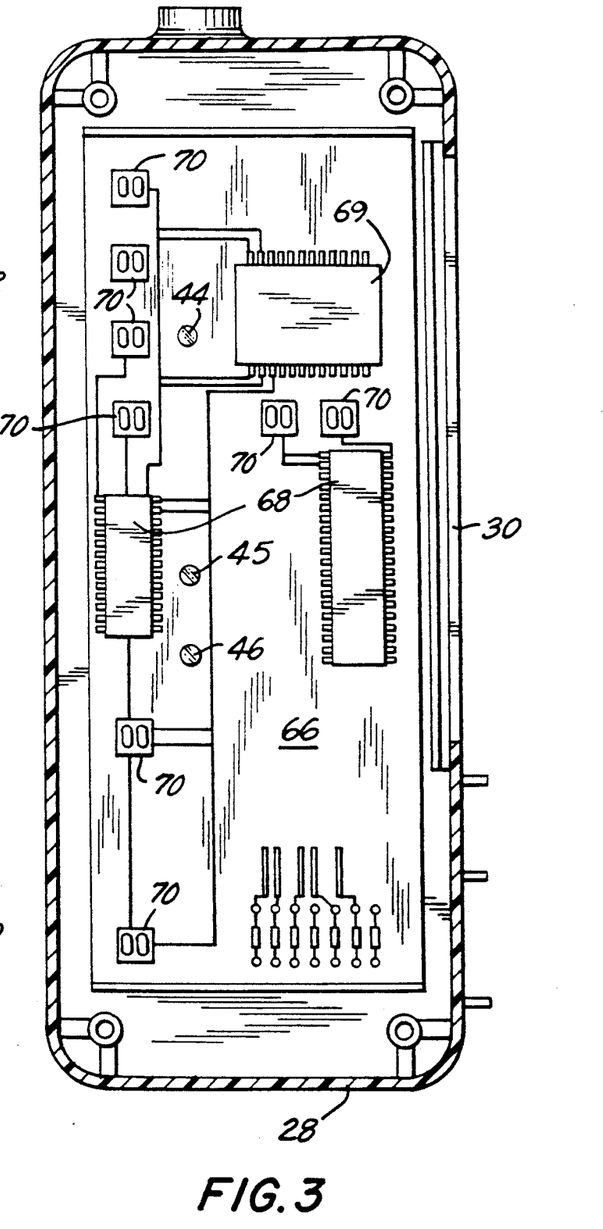
FIG. 3 is a cross sectional view of the interior components of the syringe pump, particularly illustrating one surface of the printed circuit board, as these components appear just inside the front face of the syringe pump of the present invention, taken along line 3—3 of FIG. 2.

The mechanism of actuation of the various controls on the front face 32 of the upper cover is more clearly seen by referring to FIG. 3, in conjunction with FIG. 1. The upper cover 28 carries a number of switches accessed from the front face 32 of cover 28 and these switches correspond with buttons 34, 35, 36, 38, 39, 40 and 41, respectively. Similarly, lights 44, 45 and 46 appear in FIG. 1 and have access holes.

In FIG. 3 it can be seen that there is a printed circuit board 66 mounted within upper cover 28 so that it is spaced away from front face 32. This printed circuit board includes the electrical circuitry for operation of the syringe pump and includes a variety of electrical components including one or more microprocessors 68 and/or associated integrated circuit chips, a digital readout 69 for display 42, panel lights 44, 45 and 46, and other circuits and components well within the purview of the ordinary artisan for completing the electrical functions as explained herein. Part of the circuitry on printed circuit board 66 includes switching circuits for controls 34, 35, 36, 38 and 39, and stepper circuits for controls 40 and 41. These circuits are energized by momentarily closing the circuits associated therewith, and then are de-energized by momentarily closing the circuits with the same switching mechanism.

For each control switch on the front panel of the housing, the printed circuit board includes an electrically conductive contacts 70, in this instance, composed of two electrical elements of the circuit associated therewith. Each electrically conductive contact is positioned on the printed circuit board 66 so that they are slightly spaced and directly across from a switch carried by the housing. When the user pushes with one of the controls the switch shunt moves toward electrical contacts 70 so that the circuit is completed energizing the electrical circuit affected by the control being switched. The desired operation of the selected function occurs. Similarly, with respect to control button 40 and 41, successive switching thereof cause the display to increment to the next higher number in the column associated with the button being pushed. It is observed that the electrical actuation mechanism, described above, causes the electrical circuits and functions to be energized and de-energized without the need for wire connections between the depressible control and the printed circuit board on which the circuits are maintained.

Figure 6:
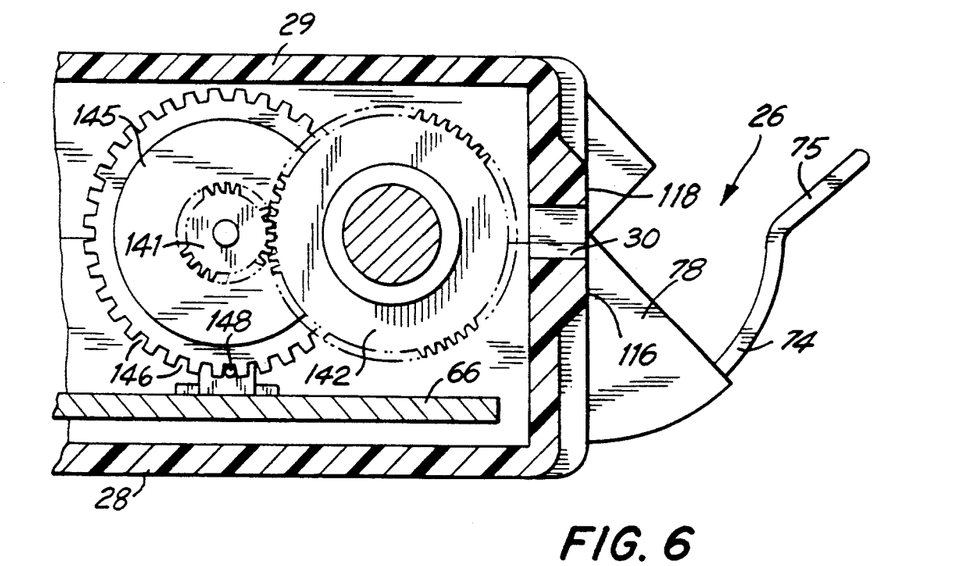
FIG. 6 is an enlarged cross-sectional view illustrating the motor mechanisms and lead screw arrangement inside the syringe housing taken along line 6—6 of FIG. 1.

Reference is now made to FIGS. 1, 2, and 6 in which the details of syringe retainer 26 are more clearly illustrated. Retainer 26 preferably includes a slidable clamp 74, which has a portion extending outside of the housing in the form of a depending arm 75 and a portion extending inside the housing in the form of a relatively flat strip. A pair of clamp guides 78 and 79, affixed to upper cover 28, hold clamp 74 in position and serve to guide the movement of the clamp for holding the syringe barrel in position with respect to the housing. Inside upper cover 28 are a pair of tracks between which the flat strip of the clamp is positioned. Thus, guide clamps 78 and 79 and tracks not only maintain the clamp in position with respect to the upper cover, but facilitate the sliding movement of the clamp in and out of the upper cover in a lateral direction across the housing. Inward bias is maintained on clamp 74 so that when the syringe barrel is held in place against the housing by virtue of depending arm 75, the inward force applied to the syringe barrel keeps the syringe barrel securely in place.

Figure 4:
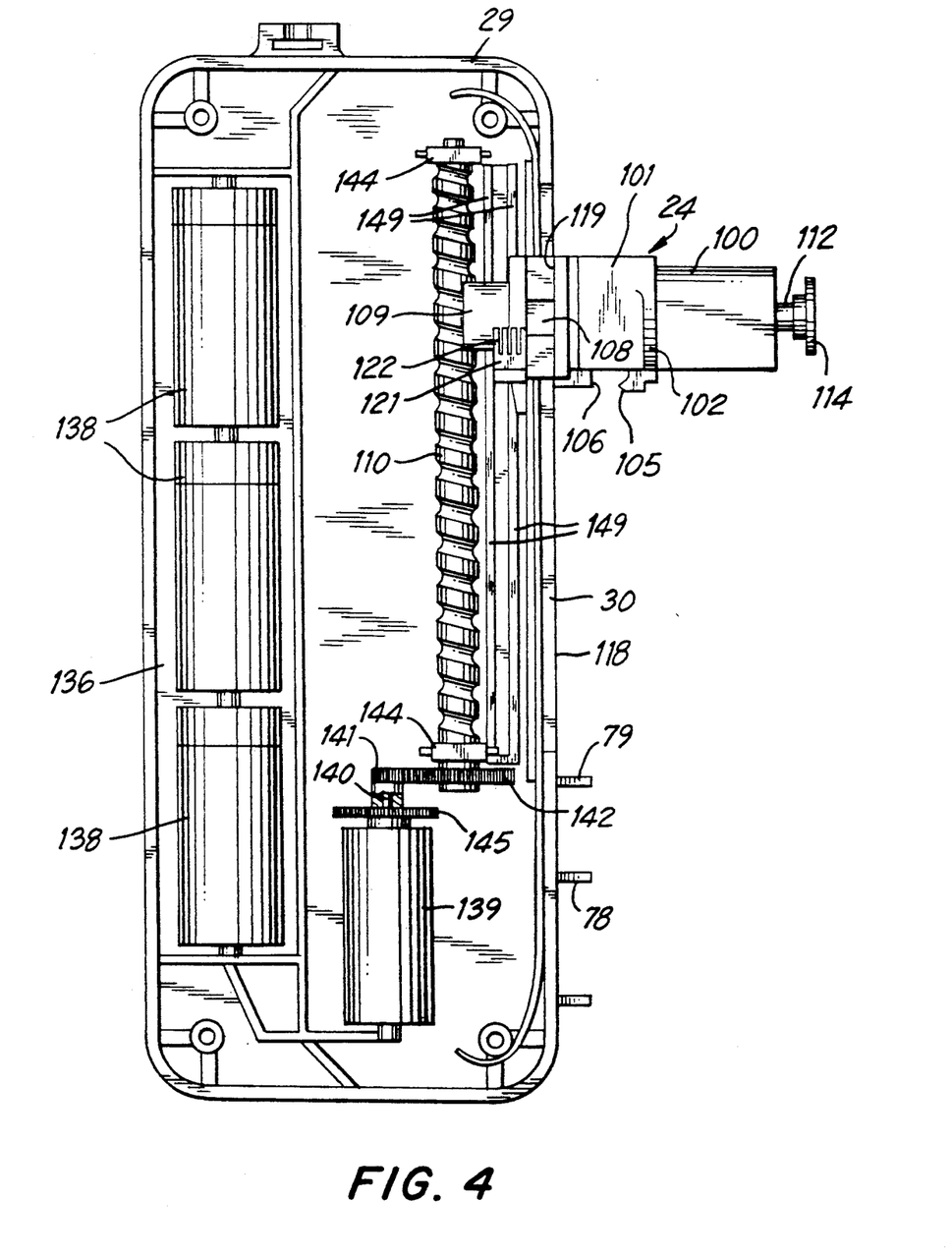
FIG. 4 is a cross-sectional view of the interior components of the syringe pump positioned below the printed circuit board as such components are positioned inside the back cover of the syringe pump housing, taken along line 4—4 of FIG. 2.
Figure 5:
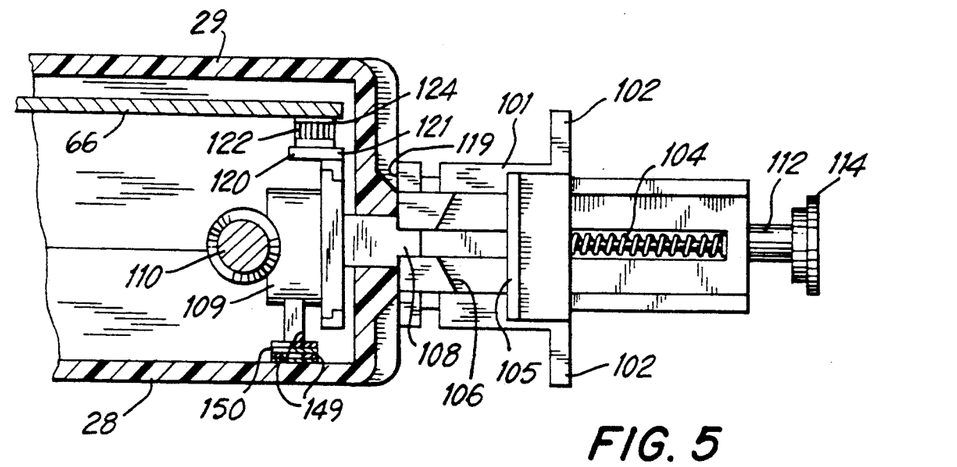
FIG. 5 is an enlarged cross-sectional view of a driver mechanism of the present invention taken along line 5—5 of FIG. 1.

FIGS. 4 and 5, along with FIGS. 1 and 2, more clearly illustrate the details of driver 24 as it is mounted on back cover 29 of housing 22. Driver mechanism 24 is an assembly including a body member 100 to which is attached a slidable latch member 101. Latch member 101 preferably has outwardly protruding finger flanges 102 for easy grasping by the user. A spring, such as coil spring 104, is preferably included within body member 100 so that a force is urged against latch member 101 keeping it biased in an inward direction toward the housing. Latch member 101 may be moved outwardly by grasping the finger flanges and applying sufficient outward force to overcome the biasing force of spring 104. In conjunction with the slidable movement of latch member 101, there is provided a catch or hook 105 which facilitates the holding of the plunger of the syringe in position against driver assembly 24. An abutment 106 is provided on body member 100 serving as a fixed element also for holding the plunger of the syringe in position against the driver assembly. Positioning of the syringe, with its extended plunger, will be described more completely hereinafter.

Body member 100 includes a shank 108 extending through slot 30 of housing 22. On the interior side and connected to shank 108 is a half-nut mechanism 109 positioned to engage the threads of a lead screw 110. When half nut 109 is engaged to lead screw 110, rotation of the lead screw imparts linear movement to driver 24 by virtue of the half nut threaded engagement. This type of driving arrangement is well known in the art of syringe pumps and no further details need be provided for a complete appreciation of the working of such elements.

In order to provide disengagement between half nut 109 and lead screw 110, a disengagement rod 112 extends through body member 100 so that is interior end is associated with half nut 109. Although not shown in FIG. 7, rod 112 is spring-loaded so that its exterior end extends a short distance beyond the end of body member 100. A thumb button 114 is preferably included at the exterior end of rod 112 so that the thumb or finger of the user may depress rod 112 inwardly. Depression of rod 112 inwardly, with sufficient force to overcome the spring-loading effect thereof, causes half nut 109 to become disengaged from lead screw 110. When disengagement of these parts occurs, driver mechanism 24 is freely slidable along slot 30 so that it may be moved to any position along the slot, such as an initial position for latching onto the plunger rod of the syringe when the syringe is being loaded. It is preferred that the depression of rod 112 for disengagement of the half-nut from the lead screw be independent of the slidable movement of latch member 101 for making the connection to the plunger rod of the syringe.

Currently available syringe pumps rely on guide rails or the like for providing bearing support to the driver mechanism as it moves in linear fashion as a result of rotation of the lead screw. Instead of guide rails, the present invention relies upon the construction of housing 22 to provide adequate bearing surfaces for supporting the driver mechanism during its linear movement along the housing. Specifically, it can be seen particularly in FIG. 5 that upper cover 28 and back cover 29 are formed so that slot 30 lies between the two housing portions when joined together. It can be seen that upper cover 28 includes a raised bearing surface 116 and back cover 29 includes a raised bearing surface 118, with each such bearing surface extending along the elongate dimension of slot 30 and running substantially parallel thereto. Bearing surfaces 116 and 118 provide a sliding support for driver mechanism 24 at portion 119 of body member 100. This support is provided at this interface when the driver mechanism is engaged to the lead screw and also when it is disengaged therefrom.

In FIGS. 4 and 5, it can be seen that a small platform 120 is mounted on the driver mechanism near the half-nut component, on the interior side of housing 22. Platform 120 is preferably an electrical insulator, such as rigid plastic or the like. Mounted on platform 120 is an electrical contact member 121 including one or more electrical contacts 122. These electrical contacts 122 are arranged so that they are in contact with one side of printed circuit board 66. One or more electrical pads 124 are provided on the surface of printed circuit board 66 so that electrical contacts 122 may come in contact therewith. Electrical pads 124 are preferably positioned on the printed circuit board at a position near the end of elongate slot 30 where the driver mechanism will finish its movement when the plunger rod has been moved all or almost all of the way into the syringe for emptying the contents thereof. Contact between electrical contacts 122 and electrical pads 124 is part of an occlusion circuit to be described more fully hereinbelow.

Turning now to FIG. 4, it can be seen that back cover 29 includes a compartment 136 which holds one or more batteries 138 to provide electrical power for operating the motor and electrical circuitry of the present syringe pump. These batteries provide direct current (DC) to a motor which is preferably a DC motor 139, for driving and rotating lead screw 110. Motor 139 includes a shaft 140, which is also illustrated in FIG. 6, taken in conjunction with FIG. 4. Attached to shaft 140 is a small gear 141 which rotates when shaft 140 rotates when the motor is operating. Another gear 142, in this case a larger gear, is connected to lead screw 110 and is in meshing engagement with smaller gear 140. Accordingly, operation of motor 139 causes the rotation of lead screw 110 by virtue of the rotating shaft of the motor and the associated gears. Lead screw 110 is maintained in position within lower housing portion 29 preferably by means of journal bearings 144 positioned at or near the respective ends of lead screw 110.

Also connected to drive shaft 140 of DC motor 139 is a wheel 145 which serves as an encoder associated with the timing and the control circuitry governing the operation of the present syringe pump. Encoder wheel 145, being connected to drive shaft 140 of the motor, therefore rotates when shaft 140 rotates. It can be seen, particularly when viewing FIG. 6, that encoder 145 is divided into a plurality of equally spaced gaps or segments 146 arranged around the periphery thereof. These gaps or segments pass in front of a light such as light emitting diode (LED) 148 connected to printed circuit boards 66, so that the number of segments may be counted for operation of the control circuit as part of the electrical circuitry hereof.

During operation of DC motor 139, for each passage of a segment 146 of the encoder past LED 148 lead screw 110 rotates to cause the drive mechanism 24 to move a fixed linear distance if everything is functioning correctly. In turn, this movement causes the movement of the syringe plunger into the syringe barrel, as will be pointed out below. As the syringe plunger is moved into the syringe barrel by a known, fixed distance, such linear movement of the plunger may be calculated by the microprocessor 68 to determine the volume delivered. Thus, it is possible to calculate the volume of liquid delivery from the syringe in milliliters per segment or increment, for each passage of a segment of the encoder. For different size syringes, this volume per increment will vary. This information of volume per increment for different size syringes, preferably of the conventional size syringes used in hospital procedures, is stored in the memory function of microprocessor 68 included in the electrical circuitry of the control functions of the present syringe pump. In connection with the microprocessor 68 and the selectable functions of the present invention, if the desired delivery rate, in milliliters per hour, is programmed or selected for operation by a user of the syringe pump, the time between increments may be determined by dividing the delivery rate (milliliters per hour) by the volume per increment (milliliters per increment). This calculation is preformed automatically by the electrical circuitry and is also storable in the memory function of the microprocessor hereof to provide the time between increments. Total volume of liquid medication to be delivered from the syringe may be established or calculated by multiplying the total number of increments of one rotation of the motor 139 by the volume per increment of the particular syringe in use. As pointed out above, each increment of the motor is determined by the passage of segment 146 of encoder 145 in conjunction with LED 148. The electrical circuitry of the present invention includes a timing circuit which is designed to account for the time intervals, to be calculated as mentioned above, associated with the desired delivery rates for different size syringes.

At the beginning of the initial timing increment of operation, DC motor 139 is turned on and a control circuit is set in accordance with the electrical circuitry thereof. Should there be a line occlusion or should the end of a cycle be reached, the force to move the plunger rod into the syringe barrel increases. This, in turn, causes the torque of the DC motor 139 to increase. Accordingly, the current increases, and at the current limiting threshold, the motor 139 stalls and stops operation. As a result, the DC motor does not complete its movement to the next segment 146 of encoder 145. In normal operation, when motor 139 reaches next encoder segment 146, it activates the electrical circuitry to turn the motor off and to reset the control circuitry. However, in the event of an occlusion which causes DC motor 139 to cease operation, the control circuitry is not reset. On the other hand, the control circuit receives the next time increment from a timing circuit in the microprocessor 68 and recognizes that the last increment has not been completed, and therefore activates the alarm circuitry. This alarm circuitry lights attention signal 46 on the front face of housing 22, and may also activate an audible alarm.

If an occlusion occurs because of fluid delivery line blockage or the like, the audible alarm is programmed to provide a rapid beeping sound or rapid flashing of light 46 on the face of the panel. If, however, the occlusion circuit is activated because of end of cycle and medication delivery from the syringe barrel has been completed, a different alarm is preferably activated. In the case of end of cycle, driver mechanism 24 has moved in linear fashion along slot 30 so that that syringe plunger is almost completely pushed within the syringe barrel. At this location, electrical contacts 122 on driver mechanism 24 come in contact with electrical pad 124 on printed circuit board 66. This contact serves as a switch or the like causing the occlusion detection circuit to issue an alarm different from the alarm mentioned above with respect to blockage in the delivery line. The end of cycle alarm may be a slow beeping signal or slow flashing of light 46 on the front panel of the housing.

It should be appreciated that the passage of segment 146 of the encoder passed LED 148 as a lead screw 110 rotates provides a signal when the movement of the segment 146 occurs. That is to say that should the motor stall or fail, the segment 146 of encoder wheel 145 permit light pass. This arrangement is such that either light passes or it does not. The microprocessor has no way of knowing where the plunger is relative to its travel, or if a failure of the lead screw 110 or half nut 109 has occurred. The only thing the microprocessor 68 can determine from encoder wheel 145 is whether or not there is rotation of wheel 145. To supplement the encoder a monitoring circuit for motion detection of driver mechanism 24 is required. The monitoring circuit is intended to inform the microprocessor and thus the operator when the medication delivery form the syringe barrel is not being pumped at the programmed rate. In particular, if the delivery of medication from the syringe is prevented or the rate of the delivery has been altered, however slightly, because of failure of the motor gearing, failure of the lead screw and half nut, restrictions in the line from the syringe to the patient or other occlusion, the monitoring circuit provides a warning.

In the specific arrangement of the preferred embodiment best shown in FIGS. 4 and 5, there is a linear potentiometer 149 carried by the housing 22 and extending substantially parallel to the lead screw 110 in the area substantially between a journal bearing 144 each positioned at a respective end of the lead screw 110. The linear potentiometer 149 is mounted inside the housing 22 on the back cover 29.

Associated with half-nut 109 which engages lead screw 110 is a contact 150. The contact 150 extends from the half-nut 109 to engage the linear potentiometer 149 and contact 150 preferably includes an electrical insulator, such as rigid plastic or the like whereby the electrically conductive strip of the linear potentiometer 149 is traversed by the contact 150 as the half-nut 109 moves along the lead screw 110. The contact 150 is connected to carry current from the conductive strip of linear potentiometer 149. In particular, the conductive strip of linear potentiometer 149 is a U-shaped path that provides electrical resistance to the flow of approximately three (3) volts. The contact 150 completes a circuit through the linear potentiometer strip such that varying resistance is seen by the contact 150 as it traverses the linear potentiometer 149. The varying resistance is directly related to the voltage drop due to resistance.

Figure 7:
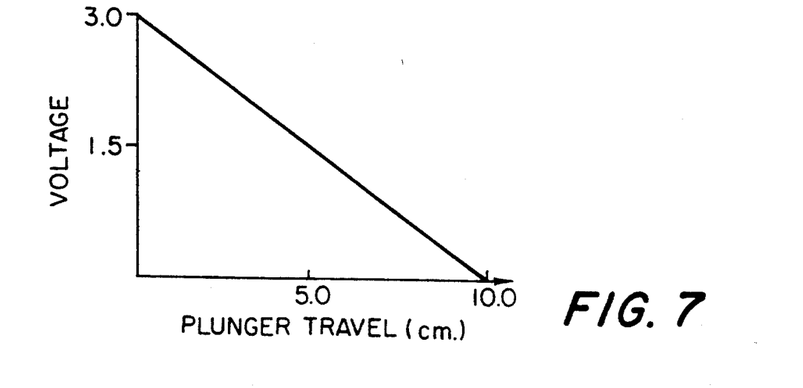
FIG. 7 is a graphical representation of the output of the linear potentiometer in terms of voltage change versus plunger travel according to the principles of the present invention.

FIG. 7 is a graph of the linear relationship of the drop in voltage and the distance traveled by contact 150 (and thus the plunger) along linear potentiometer 149. In FIG. 7 it is apparent that a drop of one (1) volt equals approximately 5 cm. of plunger travel. The U-shaped potentiometer 149 carries 3 volts across the top end and movement downwardly along the linear potentiometer 149 by the contact 150 varies the voltage drop by bridging the legs of the U thus shunting the potentiometer.

In the preferred embodiment the microprocessor 68 examines periodically the voltage variation received from the contact 150 and if there is no change in voltage, the change is inconsistent with the rotation information from the combination of the wheel 145, segments 146 and LED 148 or the change is less than a pre-programmed profile of voltage variation, set within the memory of the microprocessor 68, the alarm will be energized, thus warning the operator that a malfunction has occurred. It can be seen that a faulty drive system whether it be in the motor, the gear train or the lead screw, will be immediately noticed by the microprocessor 68, FIG. 5. Similarly, the combination of the wheel 145, segments 146 and LED 148 provide an input signal to the memory of the microprocessor 68 which includes a timer so that the rate at which the pulses of the input signal can be compared to a preset standard.

Figure 8:
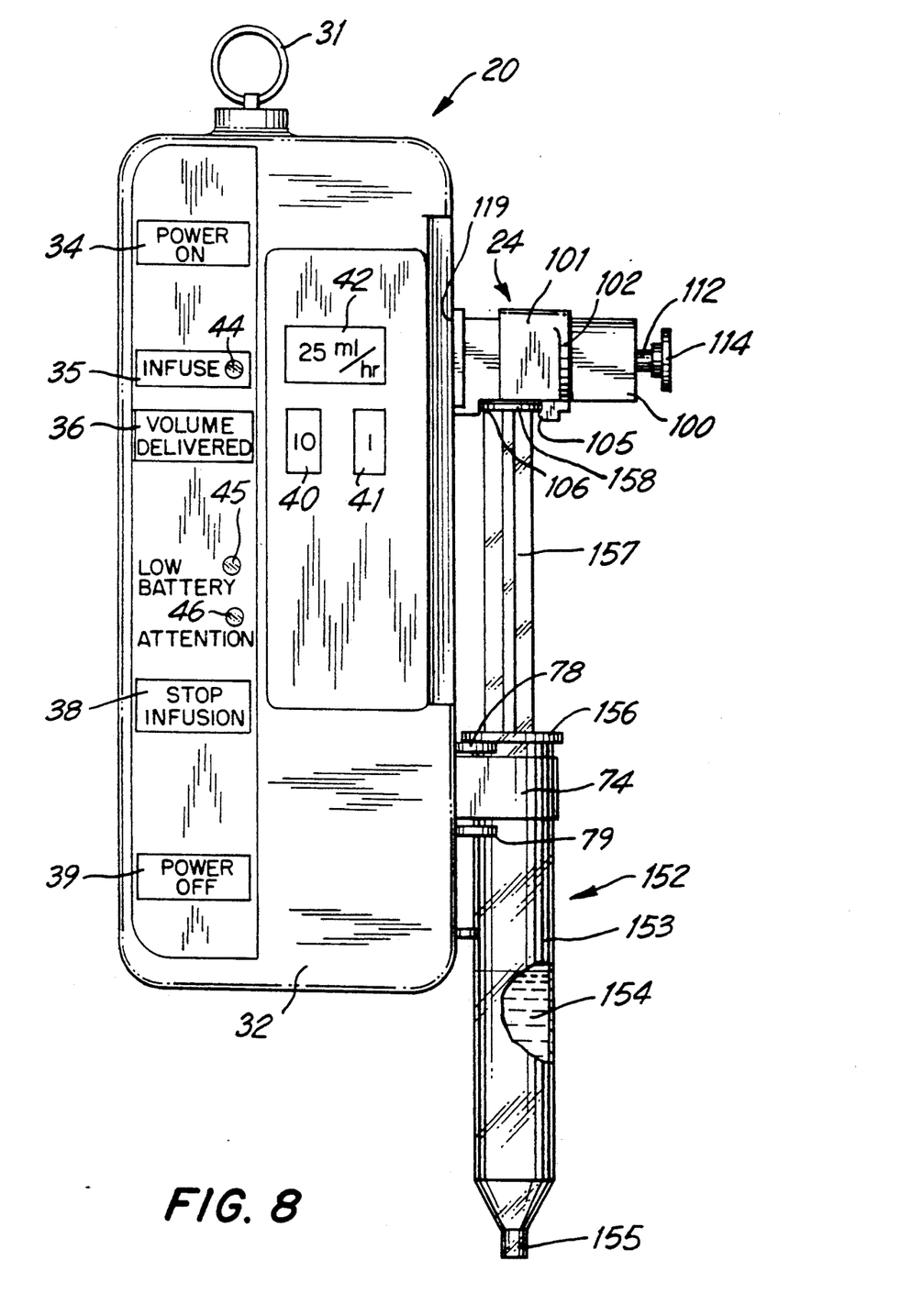
FIG. 8 is a plan view of the preferred embodiment of the syringe pump for the present invention illustrating a syringe mounted thereon as it appears in preparation for use.

The operation of syringe pump 20 will now be described in connection with FIG. 8. A syringe 152 typically is prepared with liquid medication to be delivered to a patient at a prescribed delivery rate, such as in milliliters per hour. Syringe 152 is normally of the conventional type including a syringe barrel 153 having liquid medication 154 included therein. Distal tip 155 of the syringe barrel 153 is provided for connection to a delivery line so that the liquid contents of the syringe may be passed therethrough and delivered to the patient. At the proximal end of barrel 153 there is usually a finger flange 156 on typical or conventional syringes. Extending out of the proximal end of syringe barrel 153 is a plunger 157 in the form of an elongate rod, the proximal end of which preferably terminates in a thumb disk 158 or the like.

Loaded syringe 152 is mounted onto syringe pump 20 in a few straightforward steps. The user first assures that driver mechanism clears thumb disk 158 of the syringe plunger by depressing button 114 inwardly thereby causing disengagement of the half nut form the lead screw within the interior of the housing. This disengagement allows the free movement of driver mechanism 24 to clear the plunger of the syringe. Mounting of the syringe is then facilitated by the user grasping clamp 74 and pulling same outwardly so that the clamp slides linearly between clamp guides 78 and 79. Syringe barrel 153 is then positioned so that it rests against the protruding surfaces of cradle 160 formed on the outside surfaces of upper housing portion 28 and lower housing portion 29. Arm 75 of clamp 74 is then allowed to contact the outside surface of syringe barrel 153. The clamp 74 is biased inwardly thereby holding the syringe barrel snugly and firmly in the cradle on the outside surface of the housing. At the same time, finger flange 155 at the proximal end of the syringe barrel is positioned so that it rests in contact directly on the outer surface of clamp guide 78. Accordingly, syringe barrel 153 of the syringe is now in a fixed and relatively immovable position during operation of the syringe pump.

Once the syringe barrel has been positioned as explained and the rate of delivery has been provided to the microprocessor, the apparatus is set to operate. Driver mechanism 24 is brought into engagement with thumb disk 158 by a combination of straightforward steps. Once again, button 114 may be depressed to release the internal engagement of the half nut and the lead screw so that the driver 24 may freely be slid to the position of the extending plunger rod of the syringe. Once button 114 is released, the internal engagement of the half nut and lead screw is once again established. Latch member 101 is then urged slightly outwardly by pulling on finger flanges 102. Thumb disk 158 of the syringe plunger is then slipped into engagement with abutment surface 106 on driver mechanism 24. Release of finger flanges 102 causes latch member 101 to move inwardly so that latch 105 is hooked over the protruding end of thumb disk 158 thereby capturing same in fixed position. The loaded syringe is now ready so that its contents may be delivered to the patient.

At this time, syringe pump 20 is typically hanging on a stand or the like in connection with ring 31. The user starts the procedure by first depressing POWER ON button 34 thereby activating the electrical circuitry of the syringe pump in accordance with the elements and features described. If the battery power is low, light 45 will glow; if battery power is sufficient, light 45 remains off. If, for example, the liquid contents of syringe 152 are to be delivered at the rate of 25 milliliters per hour, the user pushes "tens" button 40 for two successive increments until the number "2" appears in the tens column of display 42. In similar fashion, the "ones" button 41 is depressed until it is incremented five times whereby the number "5" appears in the ones column of display 42. Once this rate of delivery has been established and also shown on display 42, the electrical circuitry of the syringe pump, knowing the size of the syringe mounted on the housing, functions through its microprocessor capabilities to deliver the contents of the syringe at the selected rate. The monitoring circuit of the present invention is programmed to check the movement of the driver and thereby verify the delivery rate.

Having selected the desired rate of delivery, the user depresses INFUSE button 35 signaling the initiation of DC motor 139 and subsequent movement of driver mechanism 24. This movement of the driver mechanism, in turn, causes plunger 156 to be pushed into syringe barrel 152 causing the liquid medication therein to be delivered through distal tip 154 into a medication line (not shown). Display 42 may be changed to show volume delivered from the commencement of operation by depression of VOLUME DELIVERED button 36. Display 42 will then read a number in milliliters, and may be programmed to display volume for a period of a few seconds after the VOLUME DELIVERED button has been depressed. If an occlusion or decrease in delivery occurs as a result of line blockage or the like, attention light 46 is lit and an audible alarm sounds. If, however, the occlusion detection circuit is activated as a result of end of cycle when medication delivery from the syringe barrel has been completed, the DC motor stops operation and attention light 46 comes on. The visual and audible signal corresponding to end of cycle, however, is different from the signal for line occlusion. At any time during operation of the syringe pump, the user may stop the operation of the syringe pump by depressing STOP INFUSION button 38. The unit is turned off by depressing POWER OFF button 39.

Thus, the present invention provides a syringe pump with a number of significant and notable improvements over presently known and available syringe pumps. A significant safety feature for assuring delivery of life nurturing medication has been included. Most significantly, the present syringe pump may be fabricated with relatively few components and inexpensive assembly, while providing the user with sophistication of operation and versatility of performance.

What is claimed is:

1. A syringe pump comprising:
   a housing;
   a retainer mounted on the housing for receiving therein a syringe of the type including a barrel for holding liquid medication and a plunger movably positioned in the barrel for expelling the liquid medication therefrom;
   a driver movably mounted on the housing for engagement with the plunger and for pushing the plunger into the barrel to thereby force the liquid medication out of the barrel;
   a motor assembly as part of the driver for providing rotary motion and for converting the rotary motion to linear driver movement;
   control means within the housing for setting the rate of movement of the driver against the plunger to thereby regulate delivery of the liquid medication from the barrel;
   a potentiometer carried by the housing to provide an input signal for indicating the position of the driver;
   a rotary indicator associated with the motor assembly and responsive to rotary movement of a part thereof, the rotary indicator providing an additional input signal indicative of the movement of a part of the motor assembly; and
   a monitoring circuit mounted on the housing and connected with the potentiometer and the rotary indicator to receive the input signal from the potentiometer and to receive the additional input signal from the rotary indicator, the monitoring circuit comprising a processor for processing and comparing the input signal from the potentiometer and the additional input signal from the rotary indicator to detect a malfunction of the syringe pump.

2. The syringe pump of claim 1 wherein the monitoring circuit comprises a memory, the memory containing data comprising reference values as standards representative of expected positions of the driver to which the input signal from the linear potentiometer can be compared to verify that the motion of the driver during operation of the pump matches the standards.

3. The syringe pump of claim 2 further comprising a timer for verifying the rate of movement of the driver.

4. The syringe pump of claim 1 wherein the rotary indicator comprises means for producing pulses indicative of the rate of rotation of the motor, the monitoring circuit comprises means to detect the spacing between the pulses means for comparing the spacing between the pulses to verify the movement of the part of the motor assembly.

5. The syringe pump of claim 1 wherein the monitoring circuit comprises a memory, the memory containing a preset function of varying voltage as a standard to which the input signal from the potentiometer can be compared to verify the motion of the driver during operation of the pump.

* * * * *